United States Patent
Michnick et al.

(12) 
(10) Patent No.: US 6,897,017 B1
(45) Date of Patent: *May 24, 2005

(54) VIVO LIBRARY-VERSUS-LIBRARY SELECTION OF OPTIMIZED PROTEIN-PROTEIN INTERACTIONS

(75) Inventors: Stephen William Watson Michnick, Montreal (CA); Joelle N. Pelletier, Montreal (CA); Katja M. Arndt, Freiburg (DE); Andreas Pluckthun, Zürich (CH)

(73) Assignee: Odyssey Thera Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/603,885

(22) Filed: Jun. 26, 2000

Related U.S. Application Data (63) Continuation-in-part of application No. 09/017,412, filed on Feb. 2, 1998, now Pat. No. 6,270,964.
(60) Provisional application No. 60/141,210, filed on Jun. 26, 1999.

(30) Foreign Application Priority Data

Jan. 31, 1997 (CA) ................................................ 219496

(51) Int. Cl.[7] .......................... C12Q 1/68; C12N 15/52; C12P 21/02
(52) U.S. Cl. .............................. 435/6; 435/5; 435/69.7; 435/320.1; 435/DIG. 1; 435/DIG. 2; 435/DIG. 34; 435/DIG. 35; 435/DIG. 37; 536/23.1; 536/23.5
(58) Field of Search .............................. 435/5, 6, 69.1, 435/69.7, 320.1, 440, 455, 468, DIG. 1, DIG. 2, DIG. 34, DIG. 35, DIG. 37; 536/23.1, 23.5, 23.4

(56) References Cited

U.S. PATENT DOCUMENTS 6,270,964 B1 * 8/2001 Michnick et al. .............. 435/6

OTHER PUBLICATIONS

Pelletier et al., (Protein Engineering, 1997, vol. 10, p. 89).*

* cited by examiner

Primary Examiner—Padmashri Ponnaluri
(74) Attorney, Agent, or Firm—Isaac A. Angres

(57) ABSTRACT

The present invention describes a rapid and efficient in vivo library-versus-library screening strategy for identifying optimally interacting pairs of heterodimerizing polypeptides. It allows for the screening of a protein library against a second protein library, rather than against a single bait protein, and thus has numerous applications in the study of protein-protein interactions. Additionally, it allows for the application of different selection stringencies. Two leucine zipper libraries, semi-randomized at the positions adjacent to the hydrophobic core, were genetically fused to either one of two designed fragments of the enzyme murine dihydrofolate reductase (mDHFR), and cotransformed into E. coli. Interaction between the library polypeptides was required for reconstitution of the enzymatic activity of mDHFR, allowing bacterial growth. Analysis of the resulting colonies revealed important biases in the zipper sequences relative to the original libraries, which are consistent with selection for stable, heterodimerizing pairs. Using more weakly associating mDHFR fragments, we increased the stringency of selection. We enriched the best performing leucine zipper pairs by multiple passaging of the pooled, selected colonies in liquid culture, as the best pairs allowed for better bacterial propagation. This competitive growth allowed small differences among the pairs to be amplified, and different sequence positions were enriched at different rates. We applied these selection processes to a library-versus-library sample of $2.0 \times 10^6$ combinations, and selected a novel leucine zipper pair which may be appropriate for use in further in vivo heterodimerization strategies.

17 Claims, 5 Drawing Sheets

FIG. 1

(A) Library constructs (B) Single-step selection (C) Competition selection

SEQUENCE LISTING

```
<160> NUMBER OF SEQ ID NOS: 4

<210> SEQ ID NO 1
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 1

Val Ala Gln Leu Glu Glu Lys Val Lys Thr Leu Arg Ala Gln Asn Tyr
1               5                   10                  15

Glu Leu Lys Ser Arg Val Gln Arg Leu Arg Glu Gln Val Ala Gln Leu
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 2

Val Asp Glu Leu Gln Ala Glu Val Asp Gln Leu Gln Asp Glu Asn Tyr
1               5                   10                  15

Ala Leu Lys Thr Lys Val Ala Gln Leu Arg Lys Lys Val Glu Lys Leu
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 3

Val Ala Gln Leu Arg Glu Arg Val Lys Thr Leu Arg Ala Gln Asn Tyr
1               5                   10                  15

Glu Leu Glu Ser Glu Val Gln Arg Leu Arg Glu Gln Val Ala Gln Leu
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: leucine zipper-forming peptide designed from
      hybrid libraries between GCN4 and c-Jun/c-Fos

<400> SEQUENCE: 4

Val Asp Glu Leu Lys Ala Glu Val Asp Gln Leu Gln Asp Gln Asn Tyr
1               5                   10                  15

Ala Leu Arg Thr Lys Val Ala Gln Leu Arg Lys Glu Val Glu Lys Leu
            20                  25                  30
```

VIVO LIBRARY-VERSUS-LIBRARY SELECTION OF OPTIMIZED PROTEIN-PROTEIN INTERACTIONS

This application is a continuation-in-part of U.S. Ser. No. 09/017,412 filed Feb. 2, 1998, now U.S. Pat. No. 6,270,964 granted Aug. 7, 2001; the contents of which are incorporated by reference herein, and this application also claims the benefit of U.S. provisional application No. 60/141,210 filed Jun. 26, 1999.

The following abbreviations are used throughout the present specification: mDHFR, murine dihydrofolate reductase; WinZip: dominant zipper pairs obtained from competition selection; WinZip-A1B1: original pair selected, comprising peptide A1 from libraryA and peptide B1 from libraryB; WinZip-A1B2 and WinZip-A2B1: optimized pairs comprising the original partner A1 or B1 and the new partner B2 or A2, respectively.

FIELD OF THE INVENTION

Many of the problems currently being studied in molecular biology and biochemistry share a common factor: they are governed by essential molecular interactions, which are often protein-protein interactions. Important examples are the identification and functional characterization of novel gene products, the dissection of proteins into structural or functional motifs and the testing of hypotheses about the physical basis of protein-protein complementarity, whether in naturally-occuring proteins or in designed products. Our ability to address these problems has been transformed by the development of peptide- and protein-library screening techniques such as the yeast two-hybrid strategy[1,2] and phage display[3], where a library of proteins is panned against a "bait" protein. However, as the study of interacting partners is a "two-dimensional" problem influenced by variations in either partner, it would be advantageous to pan a library of proteins not against a single bait protein, but against a second library of proteins. To date, no large-scale library-vs-library selection of protein-protein interactions has been reported, because the available strategies are not amenable to this in any practical way.

The present invention describes a strategy for library-vs-library screening in intact cells based on the folding of murine enzyme dihydrofolate reductase (mDHFR) from complementary fragments[4-7]. DHFR was genetically dissected into two rationally designed fragments, each of which can be fused to a library of proteins or peptides (FIG. 1A). Members of one library which heterodimerize with a member of the other library drive the reassembly of the mDHFR fragments, resulting in reconstitution of enzymatic activity (FIG. 1B). Activity is detected in vivo using an *E. coli*-based selection assay, where the bacterial DHFR is specifically inhibited with trimethoprim, preventing biosynthesis of purines, thymidylate, methionine and pantothenate, and therefore cell division. The reconstituted mDHFR, which is insensitive to the low trimethoprim concentration present in selection, restores the biosynthetic reactions required for bacterial propagation. As a result, the interaction between library partners is directly linked to cell survival and detected by colony formation. We have previously demonstrated the utility of this strategy with GCN4 leucine zipper-forming peptides, as well as with larger heterodimerizing partner proteins[5] with $K^D$s (dissociation constants) ranging between 3 and 160 nM[8,9], although the affinity limits have not been determined.

In this study we demonstrate a large-scale library-vs-library selection based on the mDHFR fragment complementation assay: we screened two designed libraries of complementary heterodimeric coiled-coil forming sequences against each other. Our goal was to determine if the strategy would select interacting peptide pairs in which amino acids at the semi-randomized positions are similar to those observed in naturally-occuring or successfully designed coiled-coils which form stable heterodimers (see refs 10–12, for example). Further, it is not currently possible to predict sequences of coiled coil-forming peptides that will simultaneously have high stability and heterospecificity as well as advantageous in-vivo properties, such as resistance to proteases. In the present approach, the heterodimerizing peptides will have such characteristics by the nature of their selection. This is crucial to practical applications of optimal interacting heterodimers for in vivo studies of protein oligomerization, e.g. the design of bispecific miniantibodies[13].

Three selection strategies were tested here, each having a different level of stringency. In the lowest stringency selection, we screened two expressed libraries against each other in a single-step selection (FIG. 1B), thereby identifying all interacting polypeptide partners. In the second strategy, we increased the selection stringency by using a mutant DHFR fragment (Ile114Ala) which prevents stable reassembly of DHFR from its fragments[5] and should thus require more efficiently heterodimerizing, as opposed to homodimerizing, interacting partners to drive enzyme reconstitution. Finally, we introduced competitive metabolic selection, where clones obtained with the second strategy were pooled and passaged through several rounds of competition selection, in order to enrich for the optimally heterodimerizing partners.

By simultaneously screening two libraries against each other, we illustrate the advantages of screening a large, combinatorial sequence space in identifying stably heterodimerizing pairs. We partially sampled a sequence space of $1.72 \times 10^{10}$ combinations to select novel leucine zipper pairs with characteristics consistent with stable and specific heterodimerization. We directly demonstrate that the bias toward stability and specificity increased with increasing stringency of selection and observe the rate at which different sequence positions reach a consensus. Additionally, the in-vivo selection process ensures that solubility and stability toward proteolysis are essential for selection, yielding products ideally suited to in-vivo applications.

DESCRIPTION OF THE FIGURES

FIG. 1: (A) DNA constructs code for fusions between library proteins (shown as α-helical leucine zippers) and either fragment of murine DHFR (mDHFR). Fusions were created using either the wild-type or the mutant mDHFR fragment 2 (Ile114Ala), yielding LibA-DHFR[1] and LibB-DHFR[2]) or LibB-DHFR[2:I114A], respectively. (B) Principle of the mDHFR-fragment complementation assay: *E. coli* cells are cotransformed with both fusion libraries in minimal medium, in the presence of IPTG (for induction of expression) and trimethoprim (for inhibition of the bacterial DHFR). If the library proteins heterodimerize, mDHFR can fold from the individual fragments resulting in active enzyme and bacterial growth. Both mDHFR fragments must be present, and dimerization of the fused proteins is essential, in order for cell propagation to be possible. No growth is observed if any of these conditions is not fulfilled[5]. The surviving colonies are the result of "single-step selection" and can be directly analyzed by DNA sequencing. (C) "Competition selection" is undertaken by pooling colonies from (B) in selective, liquid culture (passage 0 or P0), propagating the cells and diluting into fresh selective medium for further passages. An aliquot can be plated and the resulting colonies analyzed by DNA sequencing.

FIG. 2: (A) Schematic representation of a leucine zipper pair visualized from the N-terminus illustrating e/g-interactions and the hydrophobic core formed by the a- and d-positions. (B) Distribution of residues at the semi-randomized positions throughout selection. The number of zipper pairs sequenced is given in parentheses, save "Before selection" where the theoretical distribution is reported. Each pair carries one core a-pair and 6 e/g-pairs. Neutral e/g-pairs have one or both residues as Gln. In "Competition (I114A)" only clones from P6 to P12 (not from earlier passages) were considered for analysis. Thus, 37 individual clones were identified, giving rise to 10 unique sequences due to multiple occurrence of the enriched clones. The distributions were calculated according to the frequency of sequence occurrence (n=37). (C) Leucine zipper sequences WinZip-A1 (SEQ ID NO:1), WinZip-B1 (SEQ ID NO:2), WinZip-A2 (SEQ ID NO:3) and WinZip-B2 (SEQ ID NO:4) obtained after competition selection and chain shuffling. The heptad positions (a to g) are followed by the heptad number (1 to 5). Invariant residues from GCN4 are underlined. Clear boxes indicate the semi-randomized e- and g-positions (black outline) and core a-position (a3) (grey outline). Circled residues were designed to contribute to helix capping. Shaded residues were designed for the introduction of restriction sites. Other residues are from c-Jun (LibA) or c-Fos (LibB). Arrows indicate putative e/g-interactions.

FIG. 3: Efficiency of competition in a model selection. The selection was set up by mixing known numbers of cells expressing either GCN4-DHFR[1]/GCN4-DHFR[2:I114A] fusions or one of 7 LibA-DHFR[1]/LibB-DHFR[2:I114A] pairs previously selected by single-step selection. The starting ratio was $2.9 \times 10^4$: 1(GCN4 to Lib). Competition selection was undertaken as described in FIG. 1C, and in the Experimental Protocol. The appearance of the library pairs in the pool was monitored by restriction analysis. A PvuII fragment (1138 bp) is unique to the LibB sequence of the LibB-DHFR[2] plasmid, while another (762 bp) is from pRep4 (repressor plasmid) and remains approximately constant. The bands were quantitated using the NIH Image gel analysis function to calculate the ratio of LibB/pRep4 (indicated below each lane).

FIG. 5: Sequencing profile of pools from passages of the chain shuffling WinZip-B1-DHFR[2:I114A]+LibA-DHFR [1]. Representative semi-randomized positions (see FIG. 2) were taken from a single competition experiment, such that the selection rates can be directly compared. The ratio of the individual triplet codons (central three nucleotides of each frame) was visually estimated (CAG=Gln; GAG=Glu; AAG=Lys; CGT=Arg; the equimolar random mix of the 4 codons results in the predominance of C at the first position, A at the second and G at the third). Mixed positions are marked by (NNN), positions where a single codon is dominant ($\geq 50\%$) are marked in lower case and those where the codon is clear ($\geq 90\%$) are marked in upper case. For passages 0, 2 and 8, two independent sequencing reactions were performed, which yielded identical results.

SUMMARY OF THE INVENTION

The present invention is directed to a method for identifying an interacting set of molecules comprising: (A) generating fragments of a reporter molecule which have a directly or indirectly detectable activity when associated; (B) coupling first fragments to members of a first panel of molecules; (C) coupling second fragments to members of a second panel of molecules; (D) mixing the products of B) and C); (E) directly or indirectly testing for said activity; and (F) identifying the panel members whose interaction resulted in said activity and which thus form an interacting set.

The invention is also directed to a method for identifying an interacting set of molecules comprising: (A) identifying a first and a second panel of molecules whose mutual interaction is desired to be tested; (B) coupling molecules of said first panel to first fragments of a reporter molecule; (C) coupling molecules of said second panel to second fragments of said reporter molecule; (D) mixing the products of B) and C); (E) directly or indirectly testing for said activity; and (F) identifying the panel members whose interaction resulted in said activity and which thus form an interacting set.

The invention is further directed to a method of screening multiple panels of molecules against each other to determine the ability of individual panel members to form an interacting set comprising: (A) coupling first and second fragments of a reporter molecule to different panel members; (B) mixing the products of (A); (C) testing for reporter molecule activity; and (D) identifying the panel members whose interaction results in said activity and which thus form an interacting set.

The invention also describes a method comprising directly or indirectly introducing different interacting sets into separate cell populations and identifying an interacting set that provides its host cells with a growth advantage relative to cells containing a different interacting set.

The instant invention is also directed to a method of preparing an assay system comprising: (A) identifying a first and a second panel of molecules whose mutual interaction is desired to be tested; (B) coupling molecules of said first panel to first fragments of a reporter molecule; and (C) coupling molecules of said second panel to second fragments of said reporter molecule.

The invention is also directed to an assay system comprising a first panel of molecules coupled to first fragments of a reporter molecule and a second panel of molecules coupled to second fragments of said reporter molecule.

Within the context of the present invention a panel can be a library, which is a molecularly generated collection of compounds that structurally or functionally differ from one another. A panel can also be any group of molecules purposefully chosen to test their ability to closely interact, either physically, chemically, etc., with other molecules.

DESCRIPTION OF THE PREFERRED EMBODIMENTS

We investigated a large-scale selection of dimerizing leucine zipper pairs from two designed semi-randomized libraries. These libraries are a hybrid between GCN4 and c-Jun/c-Fos (FIG. 2), where the central, core "a"-position ($a_3$) was randomized to either N or V, with equal probability, and the recurring "e" and "g" positions were randomized to Gln (neutral), Glu (acidic), Arg or Lys (basic), each with 25% probability. This was achieved by synthesizing oligonucleotides containing synthetic codon building blocks[14]; the details of the design will be published elsewhere (K. M. Arndt, J. N. Pelletier, K. M. Müller, T. Alber, S. W. Michnick and A. Plückthun, submitted). This library design allowed a number of complex optimization problems to be solved simultaneously by biological selection. At the core a-position the choice of V—V pairing, which confers higher thermodynamic stability to helix pairs, competes with N—N pairing, which confers specificity of parallel dimerization with a defined packing register and disfavors formation of antiparallel dimers and higher order oligomers[15,16]. Additionally, the importance of charged residues at the "e" and "g" positions was investigated. Formation of salt bridges between these positions of opposite monomers has been crystallographically observed[17] and has been proposed to contribute to the stability of dimer formation[18-20]. Additionally, the avoidance of unfavorable electrostatic interactions between same-charged residues may be more important in driving stable, specific interactions and avoiding the formation of homodimers[21]. Furthermore, the energy of charged-neutral interactions has been shown to be similar to that of charged e/g-pairs in several cases[18,21]. Other factors, such as contribution of e/g-residues to helix propensity and helix dipole stabilization add to the difficulty of predicting the optimal e/g-pairs in dimerization even in simple model systems. Although a restricted number of positions were semi-randomized here (4 residue types at 8 positions and 2 residue types at 1 position, resulting in $1.31 \times 10^5$ variants per library, and $1.7 \times 10^{10}$ library-vs-library combinations), a problem of extraordinary complexity was generated, making predictions of the outcome very challenging. Resolution of this problem required a powerful selection strategy, which could be rapidly performed and analyzed; to our knowledge the DHFR fragment complementation system is currently the only strategy amenable to this.

Single-step selection. The semi-randomized designed leucine zipper libraries were subcloned into the appropriate vector harboring either mDHFR fragment (FIG. 1A and Experimental Protocol). As a first step in selection of heterodimerizing leucine zippers, a single-step selection was undertaken, using the wild-type mDHFR fragments, by cotransformiing the libraries LibA-DHFR[1] and LibB-DHFR[2] and plating on selective media (FIG. 1B). This strategy applies only a low stringency of selection to the potential pairs, thus many library combinations were expected to be selected. Approximately 1.7% of the resulting ampicillin-resistant cells were doubly transformed, harboring (at least) one plasmid from each library when using 5 ng of each DNA, or 8% were doubly transformed when using 20 ng of each DNA, as seen from control transformations (calculated as described in the Experimental Protocol; data not shown). Of the doubly transformed cells which harbor no mutations or frame-shifts, approximately 35% formed colonies under selective conditions (Table 1). This result immediately demonstrates that even with relatively low stringency of selection, only a fraction of the possible combinations of the two libraries allows zipper heterodimerization leading to efficient mDHFR reassembly.

TABLE 1

Stringency of the selection steps: selection factors

| Single-step selection | | Selection Factor[a] |
|---|---|---|
| Wt mDHFR fragments (5 or 20 ng) | | 2.8 |
| I114A mDHFR fragments (5 or 20 ng) | | $1.4 \times 10^2$ |

| Competition selection | Initial Diversity | Frequency of dominant | Selection factor[c] |
|---|---|---|---|
| | | Pair at P12[b] | |
| Competition (I114A) | $3.9 \times 10^6$ | WinZipA1-B1:18/22 (82%) | $3.2 \times 10^6$ |
| Shuffling: WinZip-A1 + LibB-DHFR[2:11 14A] | $1.3 \times 10^5$ | WinZipA1-B2:4/6 (67%) | $8.7 \times 10^4$ |
| Suffling: WinZip-B1 + LibA-DHFR[1] | $1.3 \times 10^5$ | WinZipA2-B1:4/4 (100%) | $>1.3 \times 10^5$ |

[a]The selection factor in single-step selection is defined as the number of cotransfomed cells plated (considering only the 50% which give combinations with no mutations or frame-shifts), divided by the number of colonies surviving under selective conditions (see Results); average of 2 independent experiments. This value must be calculated at low DNA concentrations($\leq 20$ ng of each DNA) since the multiple cotransformations occuring at high DNA concentrations mask the actual selection factor.
[b]P12 is the 12$^{Th}$ round of serial cell passaging and competitive growth.
[c]The selection factor in competition selection is defined as the proportion of the dominant pair multiplied by the sequence diversity it was selected from.

Fourteen colonies resulting from two independent cotransformations were picked and the sequences encoding the zippers were determined. Even under these low stringency conditions there exist important sequence biases in these sequences relative to the unselected ones (FIG. 2B). A reduction in same-charged e/g-pairs from 31.3% (unselected) to 19% (selected) and an increase in opposite-charged pairs from 25% (unselected) to 31% (selected) were seen. As well, a strong enrichment of N—N pairing at the core a-position (25% unselected vs 57% selected) was observed. The characteristics that have been enriched are consistent with the selection of stable leucine zipper heterodimers.

Use of the mDHFR Ile114Ala mutation. We repeated the single-step selection, using the Ile114Ala mutant of mDHFR[4,5], in order to increase the stringency of selection. We reasoned that only library partners that form the most stable heterodimers can compensate for the reduced ability of the mDHFR(Ile114Ala) fragments to fold into active enzyme, resulting in higher enzyme activity and growth rates. When bacteria were cotransformed with LibA-DHFR [1] and LibB-DHFR[2:I114A], we observed a 50-fold decrease in the number of colonies upon selective plating compared to the wild-type DHFR fragments (Table 1). Twenty-five colonies were picked from 3 independent cotransformations and the DNA sequences were analyzed. The increase in selectivity was concomitant with an extremely strong selection for N—N pairing at the core a-position (92%; FIG. 2B), illustrating that the specificity of in-register parallel alignment provided by N—N pairing is more highly favored under these in-vivo selection conditions than the higher stability afforded by V—V pairing. Reassembly of mDHFR from its fragments requires that in the final structure, the two fragment N-termini be brought close enough together to allow native-like refolding of DHFR (FIG. 1)[5,22]. The peptide linkers that connect the library sequences to the DHFR fragments must be sufficiently flexible to allow DHFR to fold from its fragments, but not so long that any C-terminal to N-terminal orientation of the final folded leucine zipper would be allowed. As a result of this structural requirement, parallel in-register heterodimerization of the library peptides is the only configuration possible. Other biases in these sequences were also more pronounced than with the wt DHFR fragments (FIG. 2B). In particular, an additional increase in opposite-charged e/g-pairs from 31% to 37% was seen. In one case, a point-mutation resulted in a single clone (1/25) with a V-T pair at the core a-position.

Competition selection: Efficiency of selection. To further increase the selection pressure, we applied the principle of competition selection. We reasoned that, among selected zipper pairs, those which result in more stable heterodimerization will allow the most efficient enzyme reconstitution, leading to higher DHFR activity. If DHFR activity is limiting for growth, the higher activity should result in more rapid bacterial propagation, hence these cells would become enriched in a pool. Thereby, after sequential rounds of growth-competition, subtle differences in growth rate can be amplified, increasing the stringency of selection relative to the single-step selection.

Figure 3:
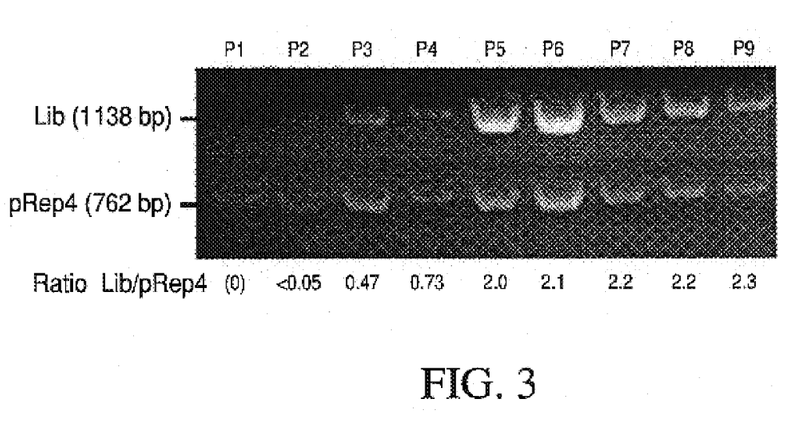

To determine the rate at which competition can enrich for particular partner pairs, we first set up a model competition with a limited number of clones as described in FIG. 1C. The initial cell mixture (P0) contained known amounts of viable cells expressing either GCN4-DHFR[1]/GCN4-DHFR[2:I114A] or one of seven LibA-DHFR[1]/LibB-DHFR[2:I114A] pairs previously obtained in a single-step selection of those libraries, mixed at a ratio of $2.9 \times 10^4$:1 (GCN4: library clones). Productive association of the homodimeric GCN4 pair should occur only 50% of the time versus up to 100% for heterodimerizing library clones, thus is disadvantaged. Within 3 passages, the library pairs were already visibly enriched (FIG. 3), and after 5 passages the measured ratio between a restriction fragment indicative of the library and a constant fragment from the repressor plasmid had reached its maximium, showing that enrichment was maximal. Colonies resulting from passage 9 (P9) were sequenced. No GCN4 leucine zippers were present among 24 sequences analyzed. Therefore, enrichment of the library pairs over GCN4 by a factor of at least $24 \times 2.9 \times 10^4 = 7 \times 10^5$ was achieved. Four out of the 7 library clones initially present survived until P9, with varying distributions (data no shown). The experiment was also repeated at a lower starting ratio of GCN4 and the same library clones were enriched, consistent with their enrichement being truly the result of selection (and not of unrepresentative sampling). This indicated that selection among the pre-selected clones was not as rapid as that seen between pre-selected and GCN4 zippers, but that the smaller differences between the pre-selected ones can still be amplified in selection. These results demonstrate that there is a direct link between reconstitution of mDHFR and growth rate.

Figure 4:
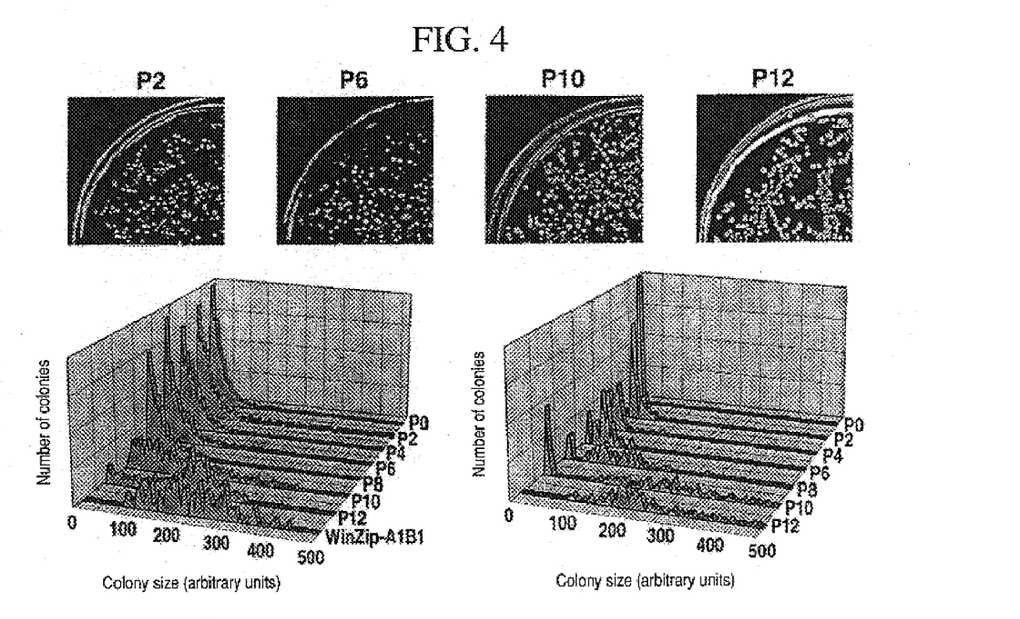
FIG. 4: Competition selection and chain shuffling. (A) Approximately $1.42 \times 10^4$ clones resulting from single-step, I114A-mutant selection were pooled (=P0) and competition selection was undertaken as described in FIG. 1C, and in the Experimental Protocol. At each passage, some cells were plated and colony sizes were quantitated. (B) Quantitation of the colony sizes from (A). For comparative purposes, quantitation of colony sizes of cells transformed with DNA of WinZip-A1B1 (but not passaged in liquid culture) is shown. (C) Quantitation of the colony sizes from passages of the chain shuffling experiment: WinZip-B 1-DHFR[2:I114A]+ LibA-DHFR[1]. In (B) and (C) the numbers of colonies were normalized such that passages could be directly compared.

Competition selection for optimal pairs: Our ultimate goal was to select for the "best" among the zipper pairs obtained by single-step selection. We obtained a large initial number of clones by cotransforming bacteria with 0.5 μg of DNA each from LibA-DHFR[1] and LibB-DHFR[2:I114A]. Approximately 50% of cells were at least doubly transformed (52% 10%, average of 2 independent control experiments, calculated as described in the Experimental Protocol). We obtained approximately $1.42 \times 10^4$ clones on selective medium, which arise from a $1.4 \times 10^2$-fold selection factor (see Table 1), and were thus selected from ($1.42 \times 10^4$) $\times$ ($1.4 \times 10^2 = 2.0 \times 10^6$ library-vs-library cotransformants. These were pooled and passaged. There was a clear increase in colony sizes with subsequent passages, indicating that faster-growing clones were taking over (FIGS. 4A, B). At P12, the colonies are homogeneously large, showing similar growth rates among the clones. Twenty-two individual colonies from P12 were picked and sequenced, as well as 11 from P10 and 2 from each previous second passage. A single pair (WinZip-A1B1, composed of WinZip-A1-DHFR[1] and WinZip-B1-DHFR[2:I114A]) was identified 18/22 times (82%) in P12, 4/11 (33%) in P10, but not in previous passages (FIG. 2C). While other sequences were found in early and late passages, none was as enriched as WinZip-A1B1. In order to verify that the growth rate recorded after competition (P12) was independant of bacteria-specific factors resulting from passaging, we cotransformed DNA from a pure clone of WinZip-A1B1 into fresh bacteria. The colony size distribution is similar for P12 and for the transformants (FIG. 4B), illustrating that the growth rate is a direct product of mDHFR reconstitution directed by the WinZip-A1B1 pair.

The sequence bias observed at the core-a position was yet stronger here: only N—N pairing was recorded at the core a-position. When the biases at the e/g-positions were calculated according to the occurrence of each sequence (n=37), there was no significant change in opposite charged pairing (37%), while a small increase in same-charged pairing was observed (from 23% to 26%) as a result of the two same-charged pair which occur in the predominant WinZip-A1B1 (FIGS. 2B, C). However, when each unique sequence was considered only once (n=10) a further increase of opposite-charged e/g-pairing was observed.

Chain shuffling of the WinZip-A1B1 sequences. In the above experiment, WinZip-A1B1 was selected from a sample representing $2.0 \times 10^6$ library-vs-library cotransformants. As the theoretical library-vs-library diversity is $(1.31 \times 10^5)^2 = 1.72 \times 10^{10}$, approximately 0.01% of the library-vs-library space was sampled. However, we obtained a very high coverage of either single library (theoretical complexity of $1.31 \times 10^5$), where the probability of all members being present at least once is P=0.973. Thus, each polypeptide sampled only a small portion of the opposite library ($2.0 \times 10^6/1.31 \times 10^5$=15.4 polypeptides of the other library with P=0.999, assuming equal transformation rates for both libraries) and it is likely that better combinations for the WinZip-A1B1 peptides may be found. Using WinZip-A1B1 as a partially optimized starting point, we combined each of the two WinZip-A1B1 polypeptides with the opposite library (WinZip-A1-DHFR[1]+LibB-DHFR[2:I114A] and WinZip-B1-DHFR[2:I114A]+LibA-DHFR[1]). Single-step selection yielded pre-selected pools for either competition. In both cases, the library ($1.3 \times 10^5$) was over-represented by a factor of 24 and 14, respectively, and the probability that all members were present at least once as partners of the "constant" peptide is $P \geq 0.999$ and 0.882, respectively. With passages of selection competition, a clear increase in colony sizes was again observed, indicating that faster-growing clones were taking over (FIG. 4C).

Figure 5:
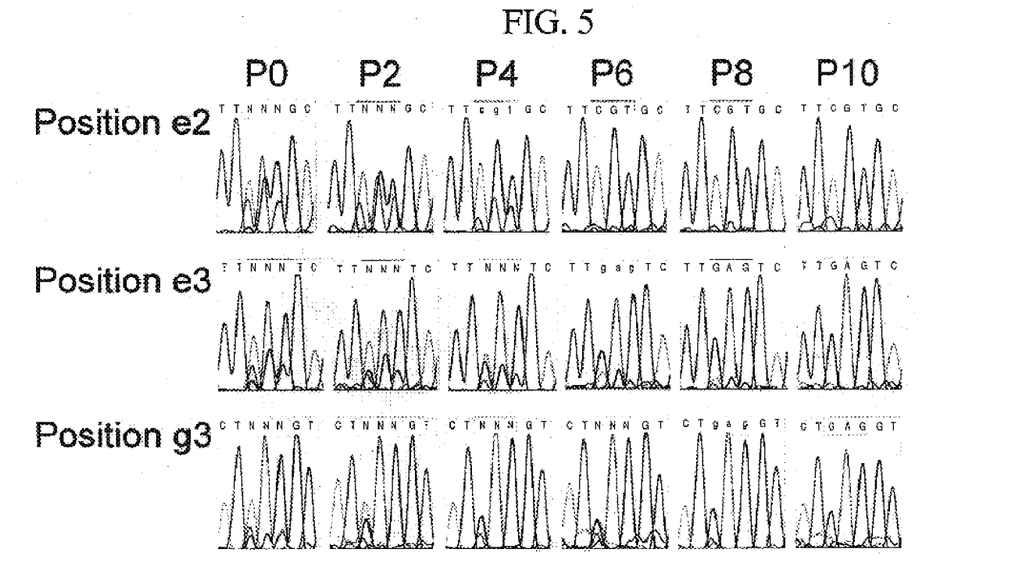

At P0 and each second passage, DNA from the entire pool of cells was sequenced in order to follow the rate of evolution of each library against a constant partner. FIG. 5 illustrates the results from representative semi-randomized positions. It is clear that the rate of selection is not constant at all positions: some positions showed a dominant residue ($\geq$50%) already at P4 and clear selection ($\geq$90%) at P6 (see position e2) while others remained mixed (<50%) until P6 and became clear only at P10 (see position g3). This was observed in both selections. The sequences from individual colonies were analyzed. In both selections, a predominant clone was identified (Table 1 and FIG. 2C), which is similar, but not identical, to the originally selected WinZip-A1B1 pair. The selection of the predominant clone WinZipA2B1 (selection of LibA-DHFR[1] against WinZip-B1-DHFR [2:I114A]) was achieved before P10, as P10 (4 clones analyzed) and P12 (4 clones analyzed) revealed only this clone. The selection of the predominant clone WinZipA1B2 (selection of LibB-DHFR[2:I 114A] against WinZip-A1-DHFR[1]) was clear but not complete after 12 passages, as it was identified 4/6 times in P12 and 3/5 times in P10.

During the multiple passages performed in competition selection, the spontaneous acquisition of trimethoprim resistance by the *E. coli* DHFR could in principle lead to a "false-positive" result, where survival would be independent of the mDHFR fragment complementation. While we observed such a phenotype on one occasion at a rate of approximately 1 resistant clone per $2 \times 10^8$ bacteria in single-step selection, we never observed this in clones resulting from competition selection, although up to $10^{12}$ cells were used during each competition. Thus this phenotype does not interfere with the selection process.

We sequenced the regions N- and C-terminal to all zipper pairs obtained, including the promoter region and part of the mDHFR-fragment coding sequence (including residue 114). As well, the entire mDHFR fragment-coding sequence was verified in all WinZip clones. In no case was a mutation, rearrangement or a recombination of any constant portion of the constructs observed. In addition, all clones were subjected to restriction analysis, and showed normal restriction patterns (data not shown). As in all in vivo strategies based on fusion proteins, we cannot preclude that the selected zippers could induce folding of mDHFR from its fragments or stabilize mDHFR through interactions of the leucine zipper with either the peptide linkers or with one or both of the DHFR fragments. However, the strong selection biases we observe, particularly the perfect selection for N—N pairing under conditions of high stringency but also of complementary e-g pairings, support our hypothesis that selection is determined by heterodimerizing leucine zipper-forming peptides.

As shown above, applicant's have applied the in-vivo mDHFR-fragment complementation assay to select stably interacting partners in a library-vs-library screen for heterodimerizing leucine zippers. Selection was successful both in single-step, and in competition assays. Many combinations of the two libraries were expected to form heterodimers, albeit of varying stability. The 2.8-fold selection factor observed in single-step selection using the wild-type mDHFR fragments is consistent with the expectation that many of the combinations should result in functional heterodimers, since 9 of the 10 a- and d-positions that define the hydrophobic core were invariant. Use of the I114A-mutant of mDHFR increased the stringency of selection 50-fold, and competition selection allowed amplification of the most successful pairs from this pool. The sequence biases observed indicate that selection favored N—N pairing very strongly over V—V pairing in the hydrophobic core, consistent with selection for specificity of parallel, in-register dimerization. This in-register alignment allows the direct comparison of the selected zippers as all helices are forced, by the N—N pair, to assume a parallel orientation, juxtaposing the same e- and g-residues in all selected library members. Opposite-charged e/g-pairs were generally, but not exclusively favored, suggesting that building stable zippers with good in-vivo performance is more complex than simply designing opposite-charged pairs. The increasing colony sizes observed during competition are consistent with selection based on higher levels of reconstituted mDHFR activity. Our results suggest that competition selection could be undertaken as a continuous culture in automated protein evolution schemes, and should be robust as we have observed no genetic instabilities. We efficiently isolated a predominant individual clone (WinZip-A1B1) from approximately $2 \times 10^6$ individual combinations, taken from a $10^{10}$ combinatorial space. The biophysical characterization of this novel leucine zipper confirms that it is stable and strongly heterodimerizing (K. M. Arndt et al., submitted). Taken with the observed sequence biases and success in growth competition, it appears that there is a direct link between stability of zipper interaction and success in the selection process. To our knowledge, this is the first demonstration of a large-scale library-vs-library selection procedure for the optimization of protein-protein interactions.

We obtained the WinZip-A1B1 pair from a partial sampling of the combinatorial space. In order to determine if WinZip-A1B1 could be improved, we performed a "chain shuffling" experiment. As each library was very well represented in this second selection, the best match within each library for the given partner should have been found. In both shuffling competitions, the population gradually converged to a predominant clone (WinZip-1A-WinZip-2B and WinZip-2A-WinZip-1B), which is similar, but not identical, to the originally selected WinZip-A1B1 pair. This indicates that the partial sampling of the $10^{10}$ sequence space yielded a good, though not optimal product (WinZip-A1B1), which was easily further improved by shuffling. The residues selected at the semi-randomized positions of these novel leucine zipper pairs differ somewhat from known natural zippers or designed zippers, yet they behaved best in this system. It is likely that other factors, such as helix-propensity and interactions of the charges with the helix dipole, also contribute to the stability. This underscores the advantages of semi-rational design accompanied by selection in an appropriate in-vivo setting.

An important insight that can be gained from varying a library against a constant partner is how the selection occurs. Two scenarios can be envisaged. In the first, the selective pressure is not equivalent at all randomized positions, such that the rate of selection is rapid at certain positions while other positions remain semi-randomized longer. In the second scenario, selective pressure is applied against each polypeptide as a whole, perhaps because the identity of a residue at one position constrains the choice at other positions within the same helix. This would result in a population where the rate of selection is independent of positional pressures arising from the partner. The results we obtain are clearly consistent with the first scenario. In particular, the core a-position showed the fastest rate of selection. While an in-depth analysis of the positional rate of selection is beyond the scope of this paper and will be presented in conjunction with the biophysical characterization of the optimized WinZip peptides (K. M. Arndt, J. N. Pelletier, K. M. Müller, S. W. Michnick, T. Alber and A. Plückthun, manuscript in preparation), we believe that the rate of selection is a reflection of the contribution of a residue at a given position, to the global coiled-coil interaction.

The DHFR-fragment complementation assay has important advantages over selection techniques such as phage display in that it is possible to perform library-vs-library screening. Furthermore, the interactions occur in vivo rather than in vitro, which is important where in vivo performance is a quality of interest. Among in vivo-based selection strategies, it has the principal advantages of being fast and simple to execute and of having a direct link between protein-protein interactions and cell propagation, thus allowing selection rather than screening. The λ-repressor dimerization strategy[23] has been applied to selection schemes similar to that presented here[15,24], but this system requires complex experimental analysis and interpretation in order to distinguish homo- from heterodimerization, and again from formation of higher-order oligomers, thus precluding thorough characterization of a large number of pairs. While library-vs-library screening should be possible using the selectively-infective phage (SIP) system[25,26], this has not yet been demonstrated. The yeast two-hybrid strategy has been very successfully applied, among other tasks, to the process of systematically mapping interactions in yeast by successive rounds against single baits[27,28]. Although there is no a priori reason for not performing library-vs-library screens with the two-hybrid strategy, with the possible exception of less efficient transformation than of E. coli, this has not been reported to date. In addition, we have previously demonstrated[5] that the DHFR-fragment complementation assay can be used as a "three-hybrid" assay[29], where a third partner is required to mediate the protein-protein interaction. In the case we presented, the third partner was a small ligand. It should be possible to extend the assay such that the third partner is either an expressed protein or a specific RNA. This library-vs-library strategy will be an invaluable tool in defining networks of interacting polypeptides in functional genomics. The current limitation of the strategy is the transformation efficiency of the E. coli strain used. Possible improvements include the use of a bacterial host with better transformation yields than BL21, or a more efficient transformation strategy.

In conclusion, the DHFR fragment complementation assay has been used in a selection strategy for library-vs-library screening of optimally-interacting leucine zippers, in an in-vivo context. The selected, heterodimerizing peptides should be appropriate for direct use in efficient protein heterodimerization strategies. The possibility of now screening two libraries against each other will allow for a much deeper exploration of complementary surfaces than is possible using a single library approach. By using a semi-rational approach for screening a large number of interacting partners in a "two-dimensional" fashion, many factors contributing to interaction specificity will be identifiable.

EXAMPLES

All reagents used were of the highest available purity. Sequencing was carried out either by cycle sequencing with fluorescence labeling (MWG-Biotech) using a LiCor detection system or by automated sequencing with an ABI sequencer. Restriction endonucleases and DNA modifying enzymes were from Pharmacia and New England Biolabs. E. coli strain XL1-Blue (Stratagene) was used for subcloning and propagation of the libraries. E. coli strain BL21 harboring the lacI[9] plasmid pRep4 (Qiagen) was cotransformed with the appropriate DNA constructs for the survival assays.

Example 1

Figure 1:
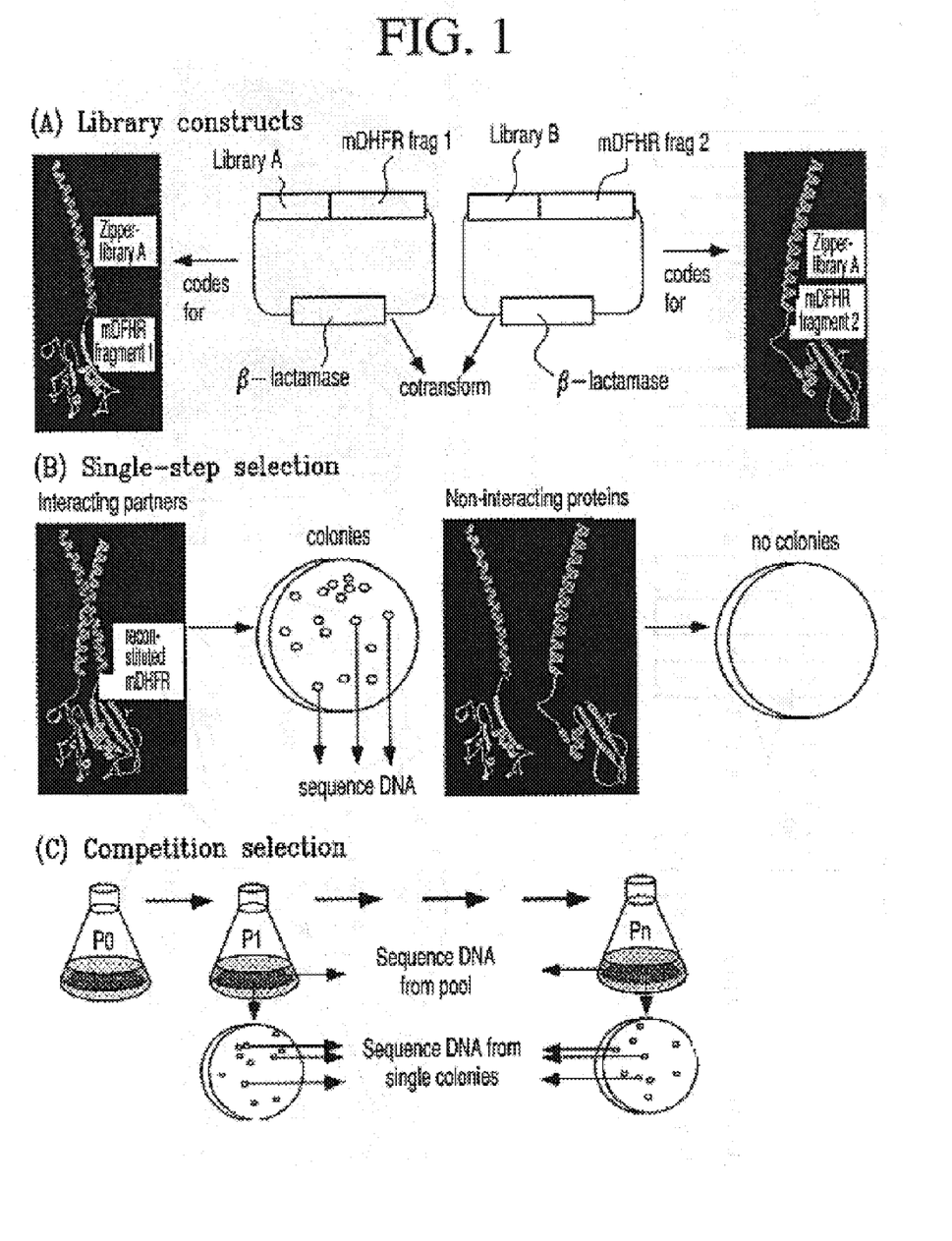
Figure 2:
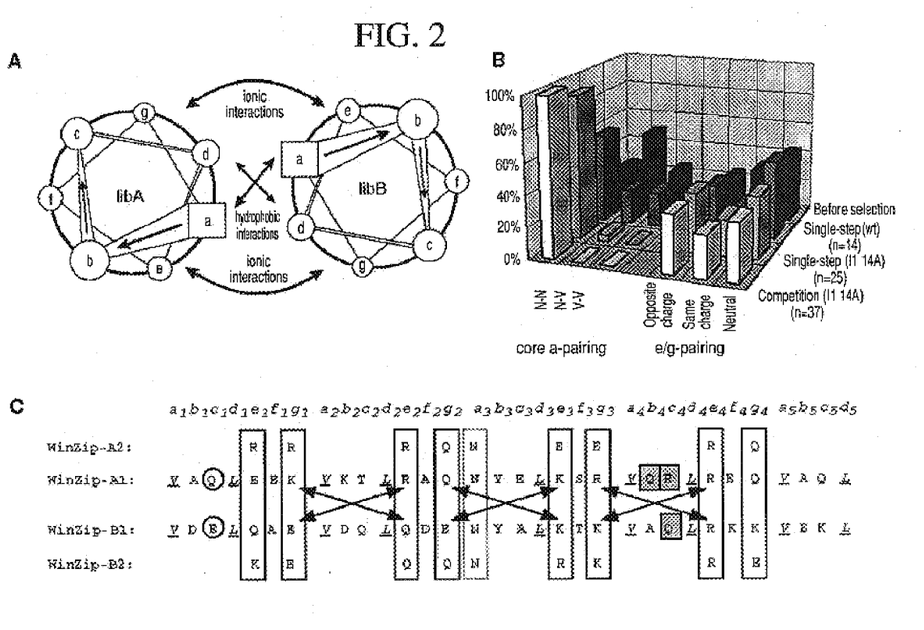

Constructs for DHFR fragment complementation: The DNA constructs encoding the N-terminal (1–107) and C-terminal (108–186) mDHFR fragments have been previously described[5]. Briefly, each fragment was amplified by PCR with appropriate unique flanking restriction sites and subcloned into a bacterial expression vector (pQE-32 from Qiagen). Each plasmid encodes an N-terminal hexahistidine tag, followed by a designed flexible linker and the appropriate DHFR fragment. Unique restriction sites between the hexahistidine tag and the flexible linker allow subcloning of the desired library. After subcloning, the resulting linker between either library and DHFR fragment was: A(SGTS)$_2$STSSGI for LibA and SEA(SGTS)$_2$STS for LibB. The design of the semi-randomized libraries is illustrated in FIG. 2 and will be described in detail elsewhere (K. M. Arndt et al., submitted). Both libraries were produced using triplet-encoding oligonucleotides[14] and amplified by PCR, using primers carrying the appropriate unique restriction sites at each terminus, and the digested, gel purified products were ligated to the appropriate vector (FIG. 1). To achieve maximal library representation, the ligation mixes were individually electroporated into XL1-Blue cells and selected with ampicillin on rich medium (LB). A 2- to 7-fold over-representation of each library was obtained. The resulting colonies were pooled and the plasmid DNA purified such that supercoiled plasmid DNA was obtained for cotransformation. In order to verify that the library populations encode the designed amino acids with the expected frequency, single clones from each library were randomly picked and sequenced before selection. No statistically significant biases were detected. Seventy to 80% of each library had no mutations or frame-shifts, and thus the library-vs-library combination yielded approximately 50% correct sequence combinations. In cotransformations, the occurrence of double transformation was calculated as the number of colonies growing under selective pressure with trimethoprim (described below) divided by the number growing in the absence, when cotransformed with equal amounts of each DNA of a given, pre-selected pair.

Example 2

Selection: Selective pressure for DHFR was maintained throughout all steps by inhibiting the bacterial DHFR with trimethoprim (1 µg/ml) in minimal medium. Ampicillin and kanamycin (100 µg/ml and 50 µg/ml, respectively) were also included in all steps to retain the library plasmids and the lacI[9] repressor-encoding plasmid (pRep4), respectively. Expression of the proteins was induced with 1 mM IPTG. When selecting on solid medium, growth was allowed for 45 hrs at 37° C. When selecting in liquid medium, the starting O.D. (600 nm) was either 0.0005 or 0.0001. Cells were propagated either in Erlenmeyer flasks or in a 10 liter New Brunswick fermentor, depending on the volume required to ensure adequate representation of all clones present, at 37° C. with shaking, or stirring at 250 RPM. After 10 to 24 hrs, O.D. (600 nm) reached 0.2 to 1.0 and cells were harvested. In competition selections, liquid culture was directly used to inoculate the next passage. We used BL21 cells with a transformation efficiency of no less than 5×10$^7$ transformants per µg of DNA using 200 pg of DNA, or 2×10$^7$ transformants per µg using 500 ng of DNA. In cotransformations, the occurrence of double transformation was calculated as the number of colonies growing under selective pressure with trimethoprim divided by the number growing in the absence, when cotransformed with equal amounts of each DNA of a given, pre-selected pair.

Example 3

Competition selection: When it was necessary to control precisely the starting number of cells in a competition, the number of viable cells in the starter cultures was quantitated as follows. The appropriate clones were propagated in liquid media under selective conditions and dilute aliquots were frozen at −80° C. with 15% glycerol. One aliquot for each clone was thawed and plated under selective conditions, and the colonies counted after 45 hrs. The volume of cells to use for P0 was then calculated, such that each clone should be over-represented by a factor of at least 2000. Colony sizes (in FIG. 4) were evaluated using the NIH Image Particle Analysis Facility.

Example 4

Chain shuffling: DNA from the WinZip-A1B1 clone was isolated and retransformed into bacteria in order to obtain clones carrying either plasmid WinZip-A1-DHFR[1] or WinZip-B1-DHFR[2:I114A]. A pure clone (for each) was electroporated with the appropriate library. Library representation was calculated by comparison with control transformations of the same cells with DNA from the other WinZip-A1B1 polypeptide (calculated as the number of colonies growing in the presence of trimethoprim divided by the number growing in the absence). Single-step and competition selection were undertaken as described above. It should be noted that cotransformation of bacteria at high DNA concentrations (0.5 $\mu$g per library) can lead to multiple plasmid transformation, where many survivors harbor more than one of either library sequence (data not shown). However, in no case was more than one sequence pair identified per clone after any competition selection, suggesting that multiply transformed cells retained only the pair of plasmids optimal for survival throughout the competition selection.

REFERENCES

1. Fields, S. & Song, O. 1989. A novel genetic system to detect protein-protein interactions. *Nature* 340, 245–246.
2. Chien, C. T., Bartel, P. L., Sternglanz, R. & Fields, S. 1991. The two-hybrid system: a method to identify and clone genes for proteins that interact with a protein of interest. *Proc. Natl. Acad. Sci. USA* 88, 9578–9582.
3. Smith, G. P. 1985. Filamentous fusion phage: novel expression vectors that display cloned antigens on the virion surface. *Science* 228, 1315–1317.
4. Pelletier, J. N., Remy, I. and Michnick, S. W. 1998. Protein-fragment complementation assays: a general strategy for the in vivo detection of protein-protein interactions. *J. Biomol. Tech.*, http://www.abrf.org/JBT/Articles/JBT0012/jbt0012.html.
5. Pelletier, J. N., Campbell-Valois, F. X. & Michnick, S. W. 1998. Oligomerization Domain-Directed Reassembly of Active Dihydrofolate Reductase From Rationally Designed Fragments. *Proc. Natl. Acad. Sci. USA* 95, 12141–12146.
6. Remy, I. & Michnick, S. W. 1999. Clonal Selection and In Vivo Quantitation of Protein Interactions with Protein Fragment Complementation Assays. *Proc Natl Acad Sci USA* 96, 5394–5399.
7. Remy, I., I. A. Wilson, and S. W. Michnick 1999. Erythropoietin receptor activation by a ligand-induced conformation change. *Science* 283, 990–993.
8. Sydor, J. R., Engelhard, M., Wittinghofer, A., Goody, R. S. & Herrmann, C. 1998. Transient kinetic studies on the interaction of Ras and the Ras-binding domain of c-Raf-1 reveal rapid equilibration of the complex. *Biochemistry* 37, 14292–14299.
9. Chen, J., Zheng, X. F., Brown, E. J. & Schreiber, S. L. 1995. Identification of an 111-kDa FKBP12-rapamycin-binding domain within the 289-kDa FKBP12-rapamycin-associated protein and characterization of a critical serine residue. *Proc. Natl. Acad. Sci. USA* 92, 4947–4951.
10. O'Shea, E. K., Lumb, K. J. & Kim, P. S. 1993. Peptide 'velcro': Design of a heterodimeric coiled coil. *Current Biology* 3, 658–667.
11. Jelesarov, I. & Bosshard, H. R. 1996. Thermodynamic characterization of the coupled folding and association of heterodimeric coiled coils (leucine zippers). *J. Mol. Biol.* 263, 344–358.
12. Zhou, N. E., Kay, C. M. & Hodges, R. S. 1994. The role of interhelical ionic interactions in controlling protein folding and stability. De novo designed synthetic two-stranded alpha-helical coiled-coils. *J. Mol. Biol.* 237, 500–512.
13. Müller, K. M., Arndt, K. M., Strittmatter, W. & Plückthun, A. 1998. The first constant domain ($C_H1$ and $C_L$) of an antibody used as heterodimerization domain for bispecific miniantibodies. *FEBS Let.* 422, 259–264.
14. Virnekas, B., Ge, L., Plückthun, A., Schneider, K. C., Wellnhofer, G. & Moroney, S. E. 1994. Trinucleotide phosphoramidites: ideal reagents for the synthesis of mixed oligonucleotides for random mutagenesis. *Nucleic Acids Res.* 22, 5600–5607.
15. Zeng, X., Herndon, A. M. & Hu, J. C. 1997. Buried asparagines determine the dimerization specificities of leucine zipper mutants. *Proc. Natl. Acad. Sci. USA* 94, 3673–3678.
16. Lumb, K. J. & Kim, P. S. 1995. A buried polar interaction imparts structural uniqueness in a designed heterodimeric coiled coil. *Biochemistry* 34, 8642–8648.
17. O'Shea, E. K., Klemm, J. D., Kim, P. S. & Alber, T. 1991. X-ray structure of the GCN4 leucine zipper, a two-stranded, parallel coiled coil. *Science* 254, 539–544.
18. Zhou, N. E., Kay, C. M. & Hodges, R. S. 1994. The net energetic contribution of interhelical electrostatic attractions to coiled-coil stability. *Protein Eng.* 7, 1365–1372.
19. Monera, O. D., Kay, C. M. & Hodges, R. S. 1994. Electrostatic interactions control the parallel and antiparallel orientation of alpha-helical chains in two-stranded alpha-helical coiled-coils. *Biochemistry* 33, 3862–3871.
20. John, M., Briand, J. P., Granger-Schnarr, M. & Schnarr, M. 1994. Two pairs of oppositely charged amino acids from Jun and Fos confer heterodimerization to GCN4 leucine zipper. *J. Biol. Chem.* 269, 16247–16253.
21. Lumb, K. J. & Kim, P. S. 1995. Measurement of interhelical electrostatic interactions in the GCN4 leucine zipper. *Science* 268, 436–439.
22. Buchwalder, A., Szadkowski, H. & Kirschner, K. 1992. A fully active variant of dihydrofolate reductase with a circularly permuted sequence. *Biochemistry* 31, 1621–1630.
23. Hu, J. C., O'Shea, E. K., Kim, P. S. & Sauer, R. T. 1990. Sequence requirements for coiled-coils: analysis with lambda repressor-GCN4 leucine zipper fusions. *Science* 250, 1400–1403.
24. Zeng, X., Zhu, H., Lashuel, H. A. & Hu, J. C. 1997. Oligomerization properties of GCN4 leucine zipper e and g position mutants. *Protein Sci.* 6, 2218–2226.
25. Spada, S. & Plückthun, A. 1997. Selectively infective phage (SIP) technology: a novel method for in vivo selection of interacting protein-ligand pairs. *Nat. Med.* 3, 694–696.
26. Rudert, F., Woltering, C., Frisch, C., Rottenberger, C. & Ilag, L. L. 1998. A phage-based system to select multiple protein-protein interactions simultaneously from combinatorial libraries. *FEBS Lett.* 440, 135–140.
27. Bartel, P. L., Roecklein, J. A., SenGupta, D. & Fields, S. 1996. A protein linkage map of *Escherichia coli* bacteriophage T7. *Nat. Genet.* 12, 72–77.
28. Fromont-Racine, M., Rain, J. C. & Legrain, P. 1997. Toward a functional analysis of the yeast genome through exhaustive two-hybrid screens. *Nat. Genet.* 16, 277–282.

29. SenGupta, D. J., Zhang, B., Kraemer, B., Pochart, P., Fields, S. & Wickens, M. 1996. A three-hybrid system to detect RNA-protein interactions in vivo. *Proc. Natl. Acad. Sci. USA* 93, 8496–8501.

We claim:

1. A method for identifying an interacting set of molecules comprising:
   A) generating first enzyme fragments and second enzyme fragments of an enzyme reporter molecule which have a directly or indirectly detectable activity when reconstituted and/or associated;
   B) coupling said first enzyme fragments to members of a first panel of molecules;
   C) coupling said second enzyme fragments to members of a second panel of molecules;
   D) mixing the products of B) and C);
   E) directly or indirectly testing for reconstitution of said enzyme activity when said enzyme fragments are associated; and
   F) identifying the panel members whose interaction resulted in said activity and which thus form an interacting set.

2. A method of claim 1 wherein said first panel comprises a library of molecules.

3. A method of claim 1 wherein at least one of said first panel and said second panel comprise a library of molecules.

4. The method of claim 1 wherein said enzyme fragments are DHFR fragments.

5. A method useful for large scale panel—panel screening for the identification of an interacting set of molecules, selected from the group consisting of interacting polypeptide partners and interacting protein partners, comprising:
   (a) generating first fragments and second fragments of a reporter enzyme which fragments have a directly or indirectly detectable activity when reconstituted and/or associated;
   (b) coupling said first enzyme fragments to members of a first panel of molecules to make first products;
   (c) coupling said second enzyme fragments to members of a second panel of molecules to make second products;
   (d) mixing said first products of step (b) and said second products of step (c);
   (e) directly or indirectly testing in vivo for reporter enzyme activity resulting from the interaction of at least one of said first products with at least one of said second products; and
   (f) identifying the interacting set of said members of said first panel and said members of said second panel associated with said first products and said second products which interacted to give said activity.

6. A method of claim 5 wherein said enzyme fragments are fragments of DHFR selected from the group consisting of fragments of wild type DHFR, fragments of rationally designed DHFR, fragments of mDHFR, and fragments of DHFR-Ile114Ala.

7. A method of claim 6 wherein said activity is enzymatic activity of DHFR.

8. A method of claim 5 wherein at least one of said first panel and said second panel comprises a library of molecules.

9. A method of claim 5 wherein at least one of said first panel of molecules and said second panel of molecules comprises leucine zipper forming peptides.

10. A method of claim 9 wherein at least one of said first panel of molecules and said second panel of molecules comprises leucine zipper forming molecules selected from the group consisting of WinZip A1 interactive peptides and WinZip B1 interactive peptides.

11. A method for identifying an interacting set of molecules comprising:
   (a) generating first fragments and second fragments of a reporter molecule which fragments have a directly or indirectly detectable activity when reconstituted and/or associated;
   (b) coupling said first fragments to members of a first panel of molecules;
   (c) coupling said second fragments to members of a second panel of molecules;
   (d) mixing the first products of step b) and the second products of step c);
   (e) directly or indirectly testing in vivo for reporter molecule activity resulting from the interaction of at least one of said first products with at least one of said second products; and
   (f) identifying the interacting subset of said members of said first panel and said members of said second panel associated with said first products and said second products which interacted to give said activity; wherein said first fragments and said second fragments are fragments of a DHFR and wherein both said first panel of molecules and said second panel of molecules comprise leucine zipper forming molecules.

12. A method of claim 11 wherein at least one of said first panel and said second panel comprises a library of molecules based on the panels of proteins selected from the group consisting of WinZip A1 interacting peptides and WinZip B1 interacting peptides.

13. A method of claim 11 wherein said fragments of DHFR are selected from the group consisting of fragments of wild type DHFR, fragments of rationally designed DHFR, fragments of mDHFR, and fragments of DHFR-Ile114Ala.

14. A method of claim 11 wherein said activity is enzymatic activity of DHFR.

15. A method for identifying highest reporter molecule activity used for identifying an interacting set of molecules comprising:
   (a) generating first fragments and second fragments of a reporter molecule which fragments have a directly or indirectly detectable activity when reconstituted and/or associated;
   (b) coupling said first fragments to members of a first panel of molecules;
   (c) coupling said second fragments to members of a second panel of molecules;
   (d) mixing the first products of step b) and the second products of step c);
   (e) directly or indirectly testing in vivo for reporter molecule activity resulting from the interaction of at least one of said first products with at least one of said second products; and
   (f) identifying the interacting subset of said members of said first panel and said members of said second panel associated with said first products and said second products which interacted to give said activity; wherein said first fragments and said second fragments are fragments of DHFR; and wherein said second fragments are selected from the group consisting of (1)DHFR fragments with lower avidity than wild type DHFR and (2) DHFR[2:I114A].

16. A method of claim 15 wherein at least one of said first panel and said second panel comprises a library of molecules.

17. A method of claim 15 wherein at least one of said first panel of molecules and said second panel of molecules comprise leucine zipper forming molecules.

* * * * *